United States Patent [19]

Hoehn

[11] 4,020,072
[45] Apr. 26, 1977

[54] 5-AMINOMETHYL-1H-PYRAZOLO[3,4-b]PYRIDINES

[75] Inventor: Hans Hoehn, Tegernheim, Germany

[73] Assignee: E. R. Squibb & Sons, Inc., Princeton, N.J.

[22] Filed: May 4, 1976

[21] Appl. No.: 682,930

[52] U.S. Cl. .................. 260/293.6; 260/268 BC; 260/296 H; 424/250; 424/263; 424/267
[51] Int. Cl.² ....................................... C07D 471/04
[58] Field of Search ...... 260/268 BC, 293.6, 296 H

[56] References Cited

UNITED STATES PATENTS

| | | | |
|---|---|---|---|
| 3,250,769 | 5/1966 | Schmidt et al. | 260/247.1 |
| 3,542,793 | 11/1970 | Rossi et al. | 260/294.8 |
| 3,810,905 | 5/1974 | Hoehn et al. | 260/295.5 B |
| 3,828,057 | 8/1974 | Denzel et al. | 260/296 H |
| 3,872,133 | 3/1975 | Fleckenstein et al. | 260/296 H |
| 3,966,746 | 6/1976 | Hoehn et al. | 260/293.6 |
| 3,983,128 | 9/1976 | Hoehn et al. | 260/296 H |
| 3,985,757 | 10/1976 | Denzel et al. | 260/294.8 C |

*Primary Examiner*—G. Thomas Todd
*Attorney, Agent, or Firm*—Lawrence S. Levinson; Merle J. Smith

[57] ABSTRACT

5-Aminomethyl-1H-pyrazolo[3,4-b]pyridines having the formula

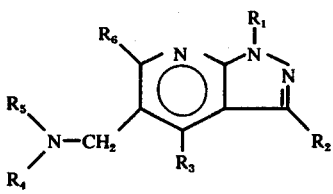

and their acid addition salts are useful as psychotropic agents.

16 Claims, No Drawings

5-AMINOMETHYL-1H-PYRAZOLO[3,4-b]PYRIDINES

SUMMARY OF THE INVENTION

This invention relates to new 5-aminomethyl-1H-pyrazolo[3,4-b]pyridines and the acid addition salts of these compounds. These new compounds have the formula (I)

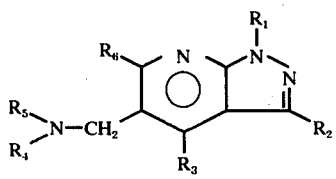

The symbols have the following meanings in formula I and throughout the specification:

$R_1$ and $R_2$ each is hydrogen, lower alkyl or phenyl, $R_3$ is hydrogen, lower alkyl, hydroxy or halogen, $R_4$ and $R_5$ each is hydrogen, lower alkyl, phenyl, di(lower alkyl)amino-lower alkyl or together they complete certain saturated unsubstituted or substituted heterocycles of 5- or 6-members, $R_6$ is hydrogen, lower alkyl- or hydroxy.

DETAILED DESCRIPTION OF THE INVENTION

The groups represented by the symbols have the following meanings throughout this specification.

The lower alkyl groups are straight or branched chain hydrocarbon groups in the series from methyl to heptyl having up to seven carbons, like methyl, ethyl, propyl, isopropyl, butyl, isobutyl, t-butyl and the like. The $C_1$–$C_4$ members are preferred and the $C_1$–$C_2$ members are especially preferred.

The halogens are the four common halogens, chlorine and bromine being preferred, especially the first.

The amino groups represented by the radical

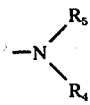

include amino, lower alkylamino groups like methylamino, ethylamino, propylamino, isopropylamino, etc., or di(lower alkyl)amino groups like dimethylamino, diethylamino, dipropylamino, methylethylamino and the like. A di(lower alkyl)amino-lower alkyl group may also be present on the nitrogen forming such groups as dimethylaminomethylamino, dimethylaminoethylamino, diethylaminomethylamino, diethylaminoethylamino, dipropylaminoethylamino, methyl(ethyl)aminoethylamino, and the like. The lower alkyl group in each of the foregoing radicals is preferably $C_1$–$C_4$ and $C_1$–$C_2$ as described above. Preferably also the

group includes only one phenyl or one di(lower alkyl)amino-lower alkyl group, i.e., $R_4$ is phenyl or di(lower alkyl)amino-lower alkyl and $R_5$ is then hydrogen. In addition, in any of the di-lower alkyl groups, preferably but not necessarily, both lower alkyl groups in a given compound are the same.

The

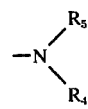

group can also represent a heterocyclic radical, wherein $R_5$ and $R_4$ join to complete the heterocycle, of the group piperidino, pyrrolidino, piperazinyl, lower alkylpiperidino, e.g., 2-, 3- or 4-methylpiperidino, (preferably 4-methylpiperidino), 2-, 3- or 4-ethylpiperidino, etc., lower alkylpiperazinyl, e.g., 4-methylpiperazin-1-yl (which is preferred), 4-ethylpiperazin-1-yl, etc., or (hydroxy-lower alkyl)piperazinyl, e.g., 4-hydroxyethylpiperazin-1-yl, and the like. In addition, the piperidino radical can form a 1,3,8-triazaspiro[4,5]decan-4-one group so that the

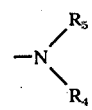

radical becomes

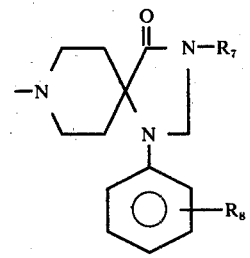

wherein $R_7$ is hydrogen or lower alkyl, and $R_8$ is hydrogen, lower alkyl or halogen.

Preferred are those compounds of formula I wherein $R_1$ and $R_2$ each is lower alkyl (especially methyl or ethyl); $R_3$ is halo (preferably chloro), hydroxy or lower alkyl (especially methyl); $R_4$ and $R_5$ each is lower alkyl (especially methyl) or together they complete the piperidino radical or the 1,3,8-triazaspiro[4,5]decan-4-one radical of formula II wherein $R_7$ is hydrogen and $R_8$ is phenyl; $R_6$ is hydrogen, hydroxy or lower alkyl (especially methyl); and physiologically acceptable acid addition salts thereof (especially the hydrochloride). The examples include an especially preferred group of compounds in addition to serving as models for other compounds included in the invention.

The new compounds of formula I can be produced by several methods. According to one procedure, a product of formula I is obtained from a compound of the formula

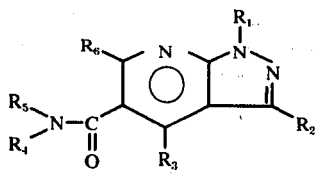
(III)

by reduction with a metal hydride such as lithium aluminum hydride or the like. See also U.S. Pat. No. 3,720,675, issued Mar. 13, 1973. According to a modification of the foregoing procedure, a product of the formula

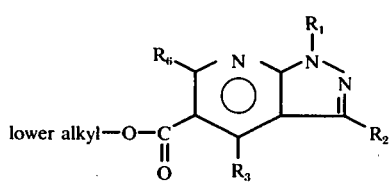
(IV)

is reduced by means of a metal hydride to give the 5-oxy-methyl compound which itself or in form of the 5-chloromethyl product reacts with amines to give derivatives of the formula I. According to another, preferred, procedure a product of formula I is obtained from a compound of the formula

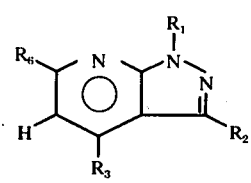
(V)

[prepared according to the procedure described in J. Heterocycl. Chem 12, 517–522 (1975)] by reaction with formaldehyde and an amine

When $R_6$ represents OH in formula V, the derivatives thereof can also exist in the pyrazolo-pyridone structure of the formula

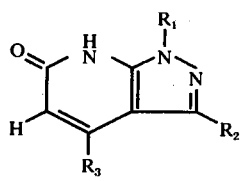
(Va)

These two isomeric structures according are included within the meaning of formula I. The compounds of formulas III and IV are formed by the following series of reactions. A 5-aminopyrazole of the formula

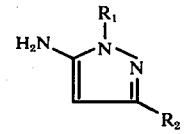
(VI)

[prepared according to the procedure described in Z.f. Chemie 10, 386–388 (1970)] is made to react with an alkoxymethylene malonic acid ester of the formula

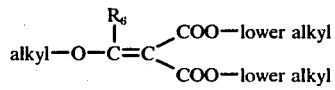
(VII)

by heating at a temperature of about 120° C.
The resulting compound of the formula

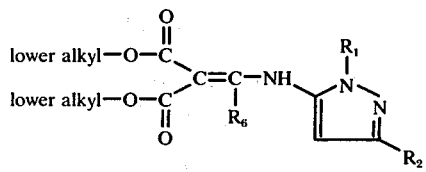
(VIII)

undergoes cyclization in an inert organic solvent such as diphenyl ether at about 230° to 260° C., while distilling off the alcohol formed, producing a compound of the formula

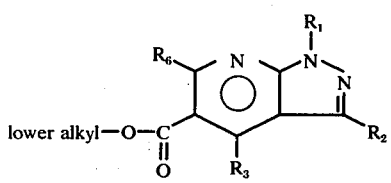
(IV)

in which $R_3$ represents hydroxy. See U.S. Pat. No. 3,629,271, issued Dec. 21, 1971.

Alternatively, instead of allowing the compound of formula VIII to undergo cyclization as described above, this product can be cyclized by treatment with a phosphorus oxyhalide like phosphorus oxychloride producing the halogenated product of the formula

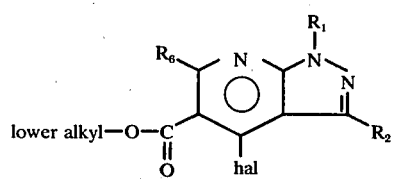
(IV)

wherein hal represents halogen, preferably chlorine.

Alternatively, a compound of formula III can also be obtained by reaction of an aminopyrazole of formula VI with an acyl malonic acid ester of the formula

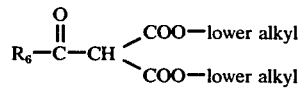
(IX)

in the presence of polyphosphoric acid at about 120° C.

When $R_1$ is hydrogen, the modified process utilizing a pyrazolo[3,4-b]pyridine having a 1-arylmethyl or 1-heteromethyl group as described in U.S. Pat. No. 3,849,411, issued Nov. 19, 1974 is followed.

The amide of formula III can be obtained from the ester (or acid chloride) of formula IV by reaction with an amine of the formula

by conventional methods.

The new compounds of formula I form salts which are also part of this invention. The salts include acid addition salts, particularly the non-toxic, physiologically acceptable members. These salts are formed by reaction with one or more equivalents of any of a variety of inorganic and organic acids providing acid addition salts including, for example, hydrohalides (especially hydrochloride and hydrobromide), sulfate, nitrate, borate, phosphate, oxalate, tartrate, malate, citrate, acetate, ascorbate, succinate or aryl- or alkanesulfonates like benzenesulfonate, methanesulfonate and toluenesulfonate, or cyclohexanesulfamate. The acid addition salts frequently provide a convenient means for isolating the product, e.g., by forming and precipitating a salt (which is not necessarily non-toxic) in an appropriate medium in which the salt is insoluble, then after separation of the salt, neutralizing with a base such as barium hydroxide or sodium hydroxide, to obtain the free base of formula I. Other salts can then be formed from the free base by reaction with one or more equivalents of acid containing the desired anion.

Additional experimental details are found in the examples.

The new compounds of this invention are pyschotropic agents and can be used as ataractic agents for the relief of anxiety and tension states, for example, in mice, cats, rats, dogs and other mammalian species. For this purpose a compound or mixture of compounds of formula I, or non-toxic, physiologically acceptable acid addition salt thereof, is preferably administered orally, but parenteral routes such as subcutaneously, intramuscularly, intravenously or intraperitoneally in the described dosages, can also be employed. A single dose, or preferably 2 to 4 divided daily doses, provided on a basis of about 1 to 50 mg. per kilogram per day, preferably about 2 to 15 mg. per kilogram per day, is appropriate.

The compounds of the invention can be utilized by formulating in compositions such as tablets, capsules or elixirs for oral administration or in sterile solutions or suspensions for parenteral administration. About 10 to 250 mg. of a compound or mixture of compounds of formula I or physiologically acceptable acid addition salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. They also serve as models for the preparation of other members of the group which can be produced by suitable substitution of starting materials. All temperatures are in degrees celsius.

EXAMPLE 1

4-Chloro-1-ethyl-3-methyl-5-(1-piperidinylmethyl)-1H-pyrazolo [3,4-b]pyridine and hydrochloride (a) [[(1-ethyl-3-methyl-5-pyrazolyl)amino]methylene]malonic acid diethyl ester 12.5 g. of 1-ethyl-3-methyl-5-aminopyrazole (0.1 mol.) and 21.6 g. of ethoxymethylene malonic acid diethyl ester (0.1 mol.) are heated to 120° (bath temperature) for 2 hours with stirring. The ethanol formed by this reaction is removed by means of a water aspirator. Vacuum distillation (b.p.$_{0.05}$ 152°–153°) yields 24.0 g. (81.5%) of a quickly crystallizing oil, [[(1-ethyl-3-methyl-5-pyrazolyl)amino]methylene]malonic acid diethyl ester, m.p. 60°–67°. The product, recrystallized from ligroin (90°–100° C), melts at 69°–70°.

(b) 1-ethyl-4-hydroxy-3-methyl-1H-pyrazolo[3,4-b]pyridine-5-carboxylic acid ethyl ester 14.8 g. of [[(1-ethyl-3-methyl-5-pyrazolyl)amino]-methylene]malonic acid diethyl ester (0.05 mol.) are dissolved in 50 g. of diphenyl ether. The reaction mixture is heated to 235°–250° (bath temperature) and allowed to react at this temperature for 1 to 2 hours, while the resulting ethanol is continuously distilled off. The last part of the alcohol is removed by means of a water aspirator. The diphenyl ether is separated by distillation with a fractionating column in vacuo. The 1-ethyl-4-hydroxy-3-methyl-1H-pyrazolo[3,4-b]pyridine-5-carboxylic acid ethyl ester is obtained at b.p.$_{0.1-0.5}$ 125°–129°, yield 10.7 g. (86%), m.p. 91°–93°. The compound is recrystallized from ligroin (90°–100°), m.p. 93°–94°.

(c) 4-chloro-1-ethyl-3-methyl-1H-pyrazolo[3,4-b]pyridine-5-carboxylic acid ethyl ester A mixture of 24.9 g. 1-ethyl-4-hydroxy-3-methyl-1H-pyrazolo[3,4-b]pyridine-5-carboxylic acid ethyl ester (0.1 mol.) and 150 ml. of phosphorus oxychloride is refluxed for 4 hours. The excess phosphorus oxychloride is removed by means of vacuum distillation. As soon as the phosphorus oxychloride has been removed, the oily residue solidifies on cooling. It is treated with water and filtered under suction (25 g., m.p. 70°–74°). The 4-chloro-1-ethyl-3-methyl-1H-pyrazolo[3,4-b]pyridine-5-carboxylic acid ethyl ester is recrystallized from cyclohexane, yield 22.8 g. (85%), m.p. 78°–79°.

(d) 4-chloro-1-ethyl-3-methyl-1H-pyrazolo[3,4-b]pyridine5-methanol 63 g. of 4-chloro-1-ethyl-3-methyl-1H-pyrazolo[3,4-b]-pyridine-5-carboxylic acid ethyl ester (0.235 mol.) are dissolved in 360 ml. of anhydrous tetrahydrofuran. Nitrogen is passed through the flask and while stirring and cooling with tap water, 5.2 g. of lithium aluminum hydride is added a bit at a time so that the reaction temperature does not exceed 25°. Stirring is continued for 2 hours at room temperature. Without further stirring, the reaction mixture is allowed to stand overnight. Then 300 ml. of 3N hydrochloric acid is added while stirring and cooling with ice water to keep the temperature between 15° and 20°. The clear solution is evaporated to dryness in vacuo, the residue is treated with 100 ml. of water and precipitated starting material (5–6 g.) is filtered off. Then the filtrate is diluted with 300 ml. of water and refrigerated overnight. The 4-chloro-1-ethyl-3-methyl-1H-pyrazolo[3,4-b]pyridine-5- methanol which crystallizes is filtered and dried at 70°, yield 32 g., m.p. 119°–121°. The compound is recrystallized from acetonitrile, m.p. 121°–122°. Acidification of the aqueous mother liquor with hydrochloric acid, evaporation in vacuo and extraction of the residue by means of boiling acetonitrile yields some starting material in form of the hydrochloride.

(e) 4-chloro-1-ethyl-3-methyl-1H-pyrazolo[3,4-b]pyridine-5-methyl chloride 475 ml. of thionyl chloride is added dropwise to 94.6 g. of 4-chloro-1-ethyl-3-methyl-1H-pyrazolo[3,4-b]pyridine-5-methanol (0.42 mol.) and the mixture is refluxed for 1½ hour. The excess thionyl chloride is removed by distillation and the residual 4-chloro-1-ethyl-3-methyl-1H-pyrazolo[3,4-b]pyridine-5-methyl chloride triturated with ligroin. Filtering off the 4-chloro-1-ethyl-3-methyl-1H-pyrazolo[3,4-b]pyridine-5-methyl chloride and recrystallization from hexane yields 89.2 g. (87%), m.p. 96°–97°.

(f) 4-chloro-1-ethyl-3-methyl-5-(1-piperidinylmethyl)-1H-pyrazolo[3,4-b]pyridine hydrochloride While stirring and cooling with tap water, 2.44 g. of 4-chloro-1-ethyl-3-methyl-1H-pyrazolo[3,4-b]pyridine-5-methyl chloride (0.01 mol.) are added in portions to 125 ml. of piperidine. Stirring is continued for an additional two hours at room temperature. Then the precipitated piperidine hydrochloride is filtered off and the filtrate is evaporated in vacuo. The oily, residual 4-chloro-1-ethyl-3-methyl-5-(1-piperidinylmethyl)-1H-pyrazolo[3,4-b]pyridine is dissolved in absolute ether and, after addition of ethereal hydrochloric acid, the precipitated 4-chloro-1-ethyl-3-methyl-5-(1-piperidinylmethyl)-1H-pyrazolo[3,4-b]pyridine, hydrochloride (1:1) is filtered off, yield 2.75 g. (84%). The product displays polymorphism and melts either at 118°–121° or 219°–220° when recrystallized from ethyl acetate/acetonitrile (about 3:1).

EXAMPLE 2

8-[(4-Chloro-1-ethyl-3-methyl-1H-pyrazolo[3,4-b]pyridin-5-yl)methyl]-1-phenyl-1,3,8-triazaspiro[4,5]decan-4-one, hydrochloride 10.6 g. of 1-ethyl-4-chloro-3-methyl-1H-pyrazolo[3,4-b]pyridine-5-methyl chloride (0.043 mol.) and 10.15 g. of 1-phenyl-1,3,8-triazaspiro[4,5]decan-4-one (0.043 mol.) dissolved in 500 ml. of dimethylformamide are heated in the presence of 4.35 g. of triethylamine at 80° for 30 hours. Then the reaction mixture is evaporated to dryness and the residue treated with water and filtered off. 1.7 g. (84%) of 8-[(4-chloro-1-ethyl-3-methyl-1H-pyrazolo[3,4-b]pyridin-5-yl)methyl]-1-phenyl-1,3,8-triazaspiro[4,5]decan-4-one, hydrochloride (1:1) are recrystallized from ethanol, m.p. 280°–281°.

EXAMPLE 3

3,6-Dimethyl-1-ethyl-5-(1-piperidinylmethyl)-1H-pyrazolo[3,4-b]pyridin-4-ol, hydrochloride, hydrate A mixture of 19.1 g. of 3,6-dimethyl-1-ethyl-1H-pyrazolo[3,4-b]pyridin-4-ol (m.p. 206°–208°), 200 ml. of dimethylformamide, 10 ml. of 40% aqueous formaldehyde (0.13 mol.) and 13 ml. of piperidine (0.13 mol.) is heated at 80° for 24 hours. Then the solution is concentrated to half of its volume in a rotary evaporator. After adding alcoholic hydrochloric acid, the solution is allowed to stand overnight at room temperature, after which time 7.4 g. of the by-product 5,5'-methylene bis[1-ethyl-1,7-dihydro-3,6-dimethyl-4H-pyrazolo[3,4-b]pyridin-4-one], hydrochloride, m.p., 297° (dec.), crystallize. To the filtrate there is added ether and the solution is allowed to stand 12 hours in a refrigerator. 11.6 g. (31%) of 3,6-dimethyl-1-ethyl-5-(1-piperidinylmethyl)-1H-pyrazolo[3,4-b]pyridin-4-ol, hydrochloride (1:2), hydrate (1:1) are obtained, m.p. 244°–245°. Recrystallization from acetonitrile elevates the melting to 245°–246°.

EXAMPLE 4

1-Ethyl-3-methyl-5-(1-piperidinylmethyl)-1H-pyrazolo[3,4-b]pyridin-4-ol, hydrochloride 32.9 g. of 4-chloro-1-ethyl-3-methyl-5-(1-piperidinylmethyl)-1H-pyrazolo[3,4-b]pyridine, hydrochloride and 320 ml. of concentrated hydrochloric acid are heated at 60° for 22 hours. Then the solution is evaporated in vacuo to dryness and the residual 33 g. of 1-ethyl-3-methyl-5-(1-piperidinylmethyl)-1H-pyrazolo[3,4-b]pyridin-4-ol, hydrochloride (1:2) are dissolved in 200 ml. of methanol while heating. Addition of 330 ml. of ether at 35° causes the solution to crystallize, yield 23 g. (67%), m.p. 276°–278° (dec.).

EXAMPLE 5

3,4-Dimethyl-1-ethyl-5-(1-piperidinylmethyl)-1H-pyrazolo[3,4-b]pyridin-6-ol, hydrochloride (a) 3,4-dimethyl-1H-pyrazolo[3,4-b]pyridin-6-ol 250.3 g. of 5-amino-1-ethyl-3-methylpyrazole (2 mol.), 260.3 g. of ethyl acetoacetate (2 mol.) and 750 ml. of glacial acetic acid are refluxed for 5 hours. On cooling overnight the crystallized 3,4-dimethyl-1H-pyrazolo[3,4-b]pyridin-6-ol is filtered off, washed with ether and dried at 100°. The white product (200 g.) melts at 236°–237°. An additional crop of 39 g. is obtained after evaporation of the mother liquor to a quarter of its volume. This portion melts at 233°–235° and can be used without further purification. A sample recrystallized from ethanol melts at 236°–237°. Total yield 293 g. (77%).

(b) 3,4-dimethyl-1-ethyl-5-(1-piperidinylmethyl)-1H-pyrazolo[3,4-b]pyridin-6-ol, hydrochloride A mixture of 47.8 g. of 3,4-dimethyl-1-ethyl-1H-pyrazolo[3,4-b]pyridin-6-ol (0.25 mol.), 37.5 ml. of aqueous 40% formaldehyde (0.5 mol.), 42.6 g. of piperidine (0.5 mol.) and 5 drops of alcoholic hydrochloric acid in 1.5 l. of dimethylformamide is heated at 85°–90° for 25 hours, while stirring. After this time, the clear solution is allowed to stand overnight in a refrigerator, yielding 61.5 g. (85%) 3,4-dimethyl-1-ethyl-5-(1-piperidinylmethyl)-1H-pyrazolo[3,4-b]pyridin-6-ol, m.p. 202°–204°.

The hydrochloric acid salt is obtained by dissolving 18 g. of 3,4-dimethyl-1-ethyl-5-(1-piperidinylmethyl)-1H-pyrazolo[3,4-b]pyridin-6-ol in 250 ml. of hot dimethylformamide and adding 10 ml. of alcoholic hydrochloric acid (332 g. HCl/l). After cooling 17.8 g. (88%) of the hydrochloride (1:1) are obtained, m.p. 291°–294° (dec.). The hydrobromide is obtained by utilizing hydrobromic acid instead of hydrochloric acid.

EXAMPLE 6

5-[(Dimethylamino)methyl]-3,4-dimethyl-1-ethyl-1H-pyrazolo[3,4-b]pyridin-6-ol, hydrochloride To a suspension of 28.7 g. of 3,4-dimethyl-1-ethyl-1H-pyrazolo[3,4-b]pyridin-6-ol (0.15 mol.) in 1 l, of dimethylformamide is added 6.75 of paraformaldehyde (0.22 mol.) and 13.5 g. of dimethylamine hydrochloride (0.165 mol.) and the mixture is heated at 80° with stirring for 22 hours. Within two hours the starting compounds become dissolved and crystallization of 5-[(dimethylamino)methyl]-3,4-dimethyl-1-ethyl-1H-pyrazolo[3,4-b]pyridin-6-ol, hydrochloride (1:1) begins, increasing after cooling, yield 25.3 g. (59%), m.p. 291°–294°. A sample, recrystallized from dimethylformamide and dried at 140°, melts at 292°–295° (dec.).

EXAMPLE 7

5-[(Dimethylamino)methyl]-3,6-dimethyl-1-ethyl-1H-pyrazolo[3,4-b]pyridin-4-ol, hydrochloride 28.7 g. of 3,6-dimethyl-1-ethyl-1H-pyrazolo[3,4-b]pyridin-4-ol (0.15 mol.), 6.75 g. of paraformaldehyde (0.22 mol.) and 13.5 g. of dimethylamine hydrochloride (0.165 mol.) suspended in 400 ml. dimethylformamide is reacted and worked up according to the procedure of Example 6 to obtain 5-[(dimethylamino)methyl]-3,6-dimethyl-1-ethyl-1H-pyrazolo[3,4-b]pyridin-4-ol, hydrochloride (1:1) yield 30.3 g. (71%), m.p. 242°–245°.

EXAMPLE 8

8-[(3,6-Dimethyl-1-ethyl-4-hydroxy-1H-pyrazolo[3,4-b]pyridin-5-yl)methyl]-1-phenyl-1,3,8-triazaspiro[4,5]decan-4-one 15.1 g. of 5-[(dimethylamino)methyl]-3,6-dimethyl-1-ethyl-1H-pyrazolo[3,4-b]pyridin-4-ol, hydrochloride (0.053 mol.) and 12.5 g. of 1-phenyl-1,3,8-triazaspiro[4,5]decan-4-one (0.053 mol.) are dissolved in 500 ml. of absolute ethanol and the clear solution is allowed to stand 3 days at room temperature. 14.35 g. (61%) of 8-[(3,6-dimethyl-1-ethyl-4-hydroxy-1-pyrazolo[3,4-b]pyridin-5-yl)methyl]-1-phenyl-1,3,8-triazaspiro[4,5]decan-4-one crystallize, m.p. 228°–230°.

The following additional compounds are produced by the procedure of the Examples indicated by appropriate substitution of the starting material having the indicated R substituent:

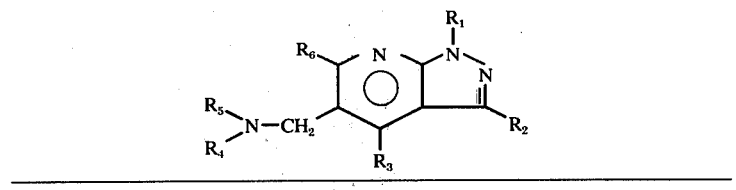

| Example | $R_1$ | $R_2$ | $R_3$ | $-N\begin{smallmatrix}R_5\\R_4\end{smallmatrix}$ | $R_6$ | Procedure of Example |
|---|---|---|---|---|---|---|
| 9 | $C_2H_5$ | $C_6H_5$ | H | $-NHCH_3$ | H | 3 |
| 10 | $CH_3$ | H | $C_2H_5$ | $-NHC_2H_5$ | $CH_3$ | 3 |
| 11 | $C_6H_5$ | $C_2H_5$ | $CH_3$ | $-N(C_2H_5)_2$ | $CH_3$ | 3 |
| 12 | H | H | OH | $-NHC_4H_9$ | H | 3 |
| 13 | H | $CH_3$ | $CH_3$ | $-N(CH_3)_2$ | OH | 6 |
| 14 | $C_3H_7$ | H | Br | $-N(C_2H_5)_2$ | $CH_3$ | 1 |
| 15 | $C_2H_5$ | $C_3H_7$ | $CH_3$ | $-N\!\!\diagup\!\!\diagdown$ (pyrrolidinyl) | $C_2H_5$ | 3 |
| 16 | $C_2H_5$ | $CH_3$ | $C_4H_9$ | $-N\!\!\diagup\!\!\diagdown\!NH$ (piperazinyl) | $CH_3$ | 3 |
| 17 | $CH_3$ | $CH_3$ | $C_2H_5$ | $-N\!\!\diagup\!\!\diagdown\!N-CH_3$ | H | 3 |
| 18 | $CH_3$ | H | Cl | $-N\!\!\diagup\!\!\diagdown\!NH$ | OH | 6 |
| 19 | $C_2H_5$ | $C_3H_7$ | Br | $-N\!\!\diagup\!\!\diagdown\!N(CH_2)_2OH$ | $CH_3$ | 3 |
| 20 | $C_3H_7$ | H | $C_2H_5$ | $-NH(CH_2)_2N(C_2H_5)_2$ | $CH_3$ | 3 |
| 21 | $C_2H_5$ | $CH_3$ | OH | $-NHCH_2N(C_2H_5)_2$ | H | 3 |
| 22 | $CH_3$ | H | $CH_3$ | $-NH(CH_2)_3N(CH_3)_2$ | $CH_3$ | 3 |
| 23 | $C_2H_5$ | $CH_3$ | $CH_3$ | $-NH(CH_2)_2N\begin{smallmatrix}CH_3\\C_2H_5\end{smallmatrix}$ | $CH_3$ | 3 |
| 24 | H | H | Cl | $-NH(CH_2)_2N(C_3H_7)_2$ | $CH_3$ | 1 |

-continued

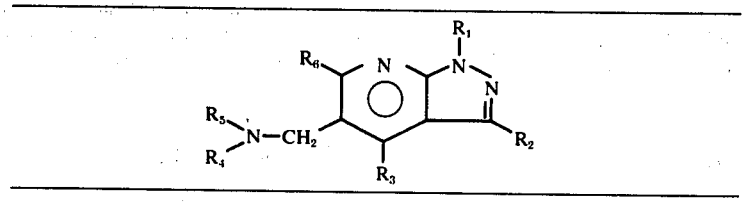

| Example | $R_1$ | $R_2$ | $R_3$ | $-N\begin{smallmatrix}R_5\\R_4\end{smallmatrix}$ | $R_6$ | Procedure of Example |
|---|---|---|---|---|---|---|
| 25 | $C_6H_5$ | H | H | N-methyl-4-methylpiperidinyl | OH | 5 |
| 26 | H | H | $CH_3$ | spiro piperidine carboxamide with N-C$_6$H$_5$ | OH | 8 |
| 27 | $CH_3$ | H | OH | spiro piperidine carboxamide with N–CH$_3$, N-C$_6$H$_5$ | $CH_3$ | 8 |
| 28 | $C_2H_5$ | $CH_3$ | Cl | spiro piperidine carboxamide with N-(4-Cl-phenyl) | H | 2 |
| 29 | H | H | $CH_3$ | spiro piperidine carboxamide with N–C$_2$H$_5$, N-(4-CH$_3$-phenyl) | $CH_3$ | 8 |
| 30 | $C_2H_5$ | $CH_3$ | Br | spiro piperidine carboxamide with N-(3-Br-phenyl) | H | 2 |
| 31 | H | $C_6H_5$ | Cl | spiro piperidine carboxamide with N–C$_6$H$_5$ | H | 2 |
| 32 | $C_3H_5$ | $CH_3$ | Cl | $-NHC_6H_5$ | OH | 5 |

-continued

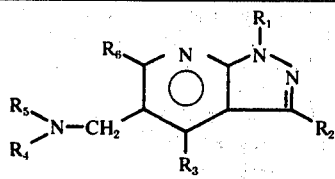

| Example | $R_1$ | $R_2$ | $R_3$ | $-N\begin{matrix}R_5\\R_4\end{matrix}$ | $R_6$ | Procedure of Example |
|---|---|---|---|---|---|---|
| 33 | H | $CH_3$ | OH | $-NHC_6H_5$ | H | 3 |
| 34 | H | H | $C_2H_5$ | $-NHC_6H_5$ | $CH_3$ | 6 |

What is claimed is:

1. A compound of the formula

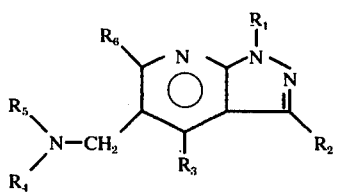

wherein $R_1$ and $R_2$ each is hydrogen, lower alkyl or phenyl;
$R_3$ is hydrogen, lower alkyl, hydroxy or halogen;
$R_4$ and $R_5$ each is hydrogen, lower alkyl, phenyl, di(lower alkyl)amino-lower alkyl or together the group

is piperidino, pyrrolidino, piperazinyl, lower alkyl-piperidino, lower alkylpiperazinyl, (hydroxy-lower alkyl)piperazinyl or

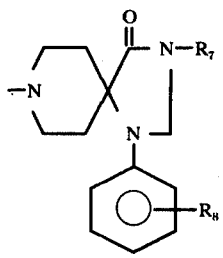

wherein
$R_7$ is hydrogen or lower alkyl and $R_8$ is hydrogen, lower alkyl or halogen;
$R_6$ is hydrogen, lower alkyl or hydroxy; and acid addition salts thereof.

2. A compound as in claim 1 wherein $R_1$ and $R_2$ each is lower alkyl; $R_3$ is halogen, hydroxy or lower alkyl; $R_4$ and $R_5$ each is lower alkyl or together complete the piperidino radical or 1-phenyl-1,3,8-triazaspiro[4,5]decan-4-one.

3. A compound as in claim 1 wherein $R_4$ and $R_5$ each is lower alkyl.

4. A compound as in claim 1 wherein

is piperidino.

5. A compound as in claim 1 wherein

is

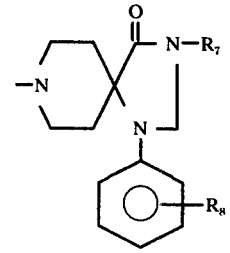

wherein
$R_7$ is hydrogen or lower alkyl; and $R_8$ is hydrogen, lower alkyl or halogen.

6. A compound as in claim 1 wherein $R_3$ is hydroxy.
7. A compound as in claim 1 wherein $R_3$ is halo.
8. A compound as in claim 1 wherein $R_3$ is lower alkyl.
9. A compound as in claim 1 wherein $R_1$ and $R_2$ each is lower alkyl and

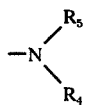

is piperidino.

10. A compound as in claim 1 wherein $R_1$ and $R_2$ each is lower alkyl and

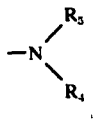

is 1-phenyl-1,3,8-triazaspiro[4,5]decan-4-one.

11. A compound as in claim 9 wherein $R_1$ is ethyl; $R_2$ is methyl; $R_3$ is chloro; and $R_6$ is hydrogen.

12. A compound as in claim 9 wherein $R_1$ is ethyl; $R_2$ and $R_6$ each is methyl; and $R_3$ is hydroxy.

13. A compound as in claim 9 wherein $R_1$ is ethyl; $R_2$ and $R_3$ each is methyl; and $R_6$ is hydroxy.

14. A compound as in claim 10 wherein $R_1$ is ethyl; $R_2$ is methyl; $R_3$ is chloro; and $R_6$ is hydrogen.

15. A compound as in claim 10 wherein $R_1$ is ethyl; $R_2$ and $R_6$ each is methyl; and $R_3$ is hydroxy.

16. A compound as in claim 1 wherein $R_1$ is ethyl; $R_2$, $R_3$, $R_4$ and $R_5$ each is methyl; and $R_6$ is hydroxy.

* * * * *